(12) United States Patent
Matsumoto et al.

(10) Patent No.: US 7,465,584 B2
(45) Date of Patent: Dec. 16, 2008

(54) METHOD AND REAGENT FOR CLASSIFYING LEUKOCYTES IN ANIMAL BLOOD

(75) Inventors: Hideaki Matsumoto, Takasago (JP); Junichi Shiraishi, Kobe (JP); Hideki Hirayama, Akashi (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 70 days.

(21) Appl. No.: 11/333,200

(22) Filed: Jan. 18, 2006

(65) Prior Publication Data

US 2006/0166366 A1 Jul. 27, 2006

(30) Foreign Application Priority Data

Jan. 24, 2005 (JP) .............................. 2005-016035

(51) Int. Cl.
*G01N 31/00* (2006.01)
*G01N 33/48* (2006.01)

(52) U.S. Cl. ................ 436/10; 436/8; 436/17; 436/63; 436/149; 436/150; 436/174; 436/175; 435/2; 252/408.1

(58) Field of Classification Search ...... 436/8, 436/10, 17, 63, 149, 150, 174, 175; 435/2; 252/408.1
See application file for complete search history.

(56) References Cited

U.S. PATENT DOCUMENTS

| | | | |
|---|---|---|---|
| 4,346,018 A | 8/1982 | Carter et al. | |
| 4,485,175 A | 11/1984 | Ledis et al. | |
| 4,745,071 A | 5/1988 | Lapicola et al. | |
| 5,116,539 A | 5/1992 | Hamaguchi et al. | |
| 5,250,437 A | 10/1993 | Toda et al. | |
| 5,316,951 A * | 5/1994 | Carver et al. | 436/63 |
| 5,486,477 A * | 1/1996 | Carver, Jr. | 436/17 |
| 5,496,734 A * | 3/1996 | Sakata | 436/63 |
| 5,686,308 A * | 11/1997 | Li et al. | 436/63 |
| 5,763,280 A | 6/1998 | Li et al. | |
| 5,786,224 A * | 7/1998 | Li et al. | 436/63 |
| 5,843,608 A * | 12/1998 | Li et al. | 436/63 |
| 5,882,933 A * | 3/1999 | Li et al. | 436/63 |
| 5,968,832 A | 10/1999 | Uchihashi et al. | |
| 6,114,130 A * | 9/2000 | Veriac et al. | 435/7.24 |
| 6,143,567 A | 11/2000 | Van Agthoven et al. | |
| 6,391,263 B1 | 5/2002 | Mishima et al. | |

FOREIGN PATENT DOCUMENTS

| | | |
|---|---|---|
| JP | 2-31162 A | 2/1990 |
| JP | 3-20667 A | 1/1991 |
| WO | WO 02/14861 A1 | 2/2002 |

OTHER PUBLICATIONS

Kazuaki Takashima, et al., "Evaluation of an Automated Blood Cell Counter (Sysmex KX-2INV) for Dogs and Cats", Journal of Animal Clinical Medicine, vol. 10, No. 3, 2001, pp. 129-134.
Peebles, D, et al, "Extended leukocyte parameters for hematology analyzers", Annals of the New York Academy of Sciences, 1986, vol. 468, 1986, XP009100510, pp. 104-112.

* cited by examiner

*Primary Examiner*—Maureen M Wallenhorst
(74) *Attorney, Agent, or Firm*—Sughrue Mion, PLLC

(57) ABSTRACT

A method for classifying leukocytes in animal blood is described. In the method, a measurement sample is prepared by mixing a canine or feline blood sample with a lysing reagent. Erythrocytes are lysed and leukocytes are shrunk in the measurement sample. The data correlated with the size of leukocytes in the measurement sample are measured. The leukocytes, on the basis of the measured data, are classified into a first group containing lymphocytes, a second group containing neutrophils and monocytes and a third group containing eosinophils.

21 Claims, 13 Drawing Sheets

METHOD AND REAGENT FOR CLASSIFYING LEUKOCYTES IN ANIMAL BLOOD

BACKGROUND OF THE INVENTION

1. Field of the Invention

The present invention relates to a method and reagent for classifying leukocytes in animal blood.

2. Description of the Related Art

In treatment or diagnosis of canine and feline diseases, blood examination is an essential examination. Information useful for treatment or diagnosis of leukemia, infections and allergic diseases is obtained in examination of leukocytes, and information useful for treatment and diagnosis of anemia is obtained in examination of hemoglobin.

The method of measuring human leukocytes has already been established. In the method, a lysing reagent is added to a human blood sample to lyse erythrocytes in the sample, and the remaining leukocytes are counted with a hemocytometer. By devising ingredients of the lysing reagent, it is possible not only to count total leukocytes, but also to classify the leukocytes into a plurality of sub-groups and count leukocytes in a specific sub-group (see, for example, U.S. Pat. Nos. 4,346,018, 4,485,175 and 5,116,539 and Japanese Laid-Open Patent Application Publication Nos. H02-031162 and H03-020667). Alternatively, a plurality of aliquots are prepared from a blood sample, and different lysing reagents are added to the respective aliquots, to measure specific sub-groups of leukocytes, and from the obtained results, the leukocytes can be classified into 5 sub-groups.

In measurement of hemoglobin, a cyan methemoglobin method is used as an international standard method. However, the cyan methemoglobin method makes use of a toxic cyan compound, thus making disposal of waste-fluid necessary. Therefore, in recent years, hemoglobin is also measured by a method of using no cyan compound; for example, SLS hemoglobin method, methemoglobin method etc. (see, for example, U.S. Pat. Nos. 5,250,437 and 5,968,832).

A hemocytometer for animal blood has been commercially available. In the hemocytometer, a reagent for human blood is used, and a program for analysis is altered to suit an animal species to be measured (see, for example, U.S. Pat. No. 6,391,263).

When a quaternary ammonium salt-containing lysing reagent for human blood is used to measure a canine or feline blood sample by an electric resistance detection method, the distribution of leukocyte sizes appears as a single peak, so the erythrocytes cannot be classified into a plurality of sub-groups (see, for example, WO 2002/014861, J. Anim. Clin. Med., 10(3) 129-134, 2001). This is because canine or feline leukocytes are fragile and sensitive to the quaternary ammonium salt as compared with human leukocytes.

To cope with this problem, WO 2002/014861 supra describes a method of measuring leukocytes by using the quaternary ammonium salt at a lower concentration than that for human blood (that is, the concentration of the salt in a solution measured for leukocytes is 1.5 to 4.5 g/L). It is described therein that according to this method, leukocytes in a blood sample such as a canine or feline sample can be classified into 3 sub-groups, that is, lymphocytes, "mixed cell group" composed mainly of monocytes, and granulocytes.

However, the method described in WO 2002/014861 supra cannot classify eosinophils into a sub-group by distinguishing them from other leukocytes. In examination of leukocytes, the number of eosinophils is information useful for diagnosis of allergic diseases and parasitosis. Particularly, canine and feline parasitosis is well known in the field of pet, and canine and feline allergic diseases are rapidly increasing in recent years. For diagnosis of allergic diseases and parasitosis for canine and feline, therefore, it is important that in blood examination, eosinophils be classified by distinguishing them from other leukocytes.

When the present inventors compared a result obtained by the method described in WO 2002/014861 supra with a result obtained by a visual examination, the correlation therebetween was low.

SUMMARY OF THE INVENTION

The object of the present invention is to provide a method and reagent for classifying leukocytes contained in a canine or feline blood sample into 3 groups by distinguishing eosinophils from other leukocytes.

A first aspect of the present invention relates to a method for classifying leukocytes in animal blood, comprising the steps of: preparing a measurement sample by mixing a canine or feline blood sample with a lysing reagent, wherein erythrocytes are lysed and leukocytes are shrunk in the measurement sample; measuring data correlated with the size of leukocytes in the measurement sample; and classifying the leukocytes, on the basis of the measured data, into a first group containing lymphocytes, a second group containing neutrophils and monocytes and a third group containing eosinophils.

A second aspect of the present invention relates to a lysing reagent for classifying leukocytes in a canine or feline blood sample into a first group containing lymphocytes, a second group containing neutrophils and monocytes and a third group containing eosinophils, comprising: a quaternary ammonium salt lysing erythrocytes and shrinking leukocytes in the blood sample, and an aqueous solvent dissolving the quaternary ammonium salt, wherein the concentration of the quaternary ammonium salt is a concentration satisfying the following conditions: (1) erythrocytes are sufficiently lysed, and (2) leukocytes are shrunk such that the leukocytes can be classified, on the basis of their size, into the first, second and third groups.

DESCRIPTION OF THE PREFERRED EMBODIMENTS

First, the present inventors measured human, canine and feline blood samples with a lysing reagent for human blood and then compared classification results of erythrocytes (Example 1). In the Example 1, a blood sample from dog was used as the canine blood sample, and a blood sample from a cat was used as a feline blood sample.

EXAMPLE 1

On the basis of a description of U.S. Pat. No. 5,968,832, the present inventors prepared a lysing reagent (lysing reagent 1) capable of classifying human leukocytes into 3 sub-groups, that is, lymphocytes, neutrophils and other leukocytes.

The composition of the lysing reagent 1 is as follows:

| Lysing reagent 1 | |
|---|---|
| Lauryl trimethyl ammonium chloride | 7.9 g/L (30 mM) |
| Stearyl trimethyl ammonium chloride | 0.84 g/L (2.4 mM) |
| Sodium chloride | 4.13 g |
| Succinic acid | 3.0 g |
| EDTA-2K | 2.5 g |
| Sodium hydroxide | 1.55 g |
| Purified water | 1 L | pH 5.3

Using the lysing reagent 1, human, dog and cat blood samples were measured with an automatic hemocytometer pocH-100iV (Sysmex Corporation). In this hemocytometer, a blood sample is diluted with a diluent poch-pack D (Sysmex Corporation) to prepare a sample diluted 500-fold. Then, one volume of the lysing reagent 1 is added to two volumes of the diluted sample to prepare a measurement sample. Thirteen seconds after the lysing reagent is added, leukocytes are counted for 6 seconds in a detector in an electric resistance system. In this example, the measured signal was transmitted from the detector via an RS-232C cable to a personal computer, and from the inputted signal, the count and the particle-size distribution were analyzed.

A smear was prepared from the blood sample used in measurement and then subjected to May-Grünwald-Giemsa staining, and the leukocytes were visually classified and counted.

Figure 1:
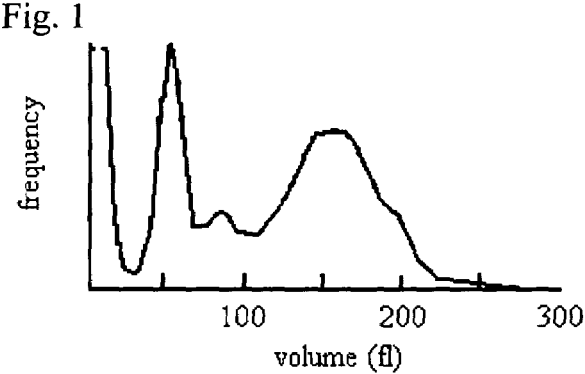
FIG. 1 shows the particle size distribution obtained by measuring a human blood sample with a lysing reagent 1 in Measurement Example 1.
Figure 2:
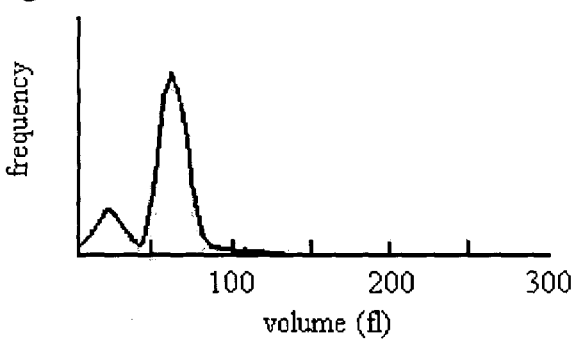
FIG. 2 shows the particle size distribution obtained by measuring a dog blood sample with a lysing reagent 1 in Measurement Example 1.
Figure 3:
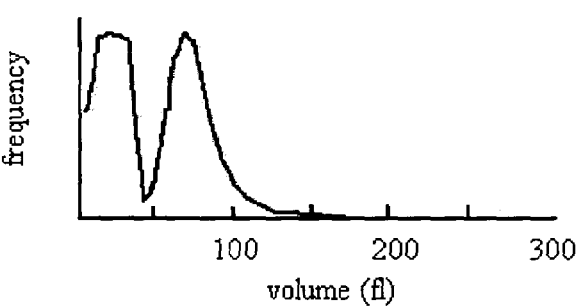
FIG. 3 shows the particle size distribution obtained by measuring a cat blood sample with a lysing reagent 1 in Measurement Example 1.

FIG. 1 shows the particle size distribution obtained by measuring a human blood sample. FIG. 2 shows the particle size distribution obtained by measuring a dog blood sample. FIG. 3 shows the particle size distribution obtained by measuring a cat blood sample. The correspondence between each sub-group on the particle size distribution and each sub-group of leukocytes can be confirmed by comparing data classified by the visual examination with data measured by the method of using the lysing reagent described above.

Similar to a description of U.S. Pat. No. 5,968,832, a group containing lysed erythrocytes, a group containing lymphocytes, a group containing neutrophils, and a group containing other leukocytes appeared from the left to right in the particle size distribution in FIG. 1. In FIGS. 2 and 3, on the other hand, a group of lysed erythrocytes and a group containing leukocytes appeared from the left to right. From FIGS. 1 to 3, it was found that the lysing reagent 1 can classify human leukocytes into 3 sub-groups, but cannot classify dog or cat leukocytes into sub-groups. It was thus found that when the lysing agent for human is used in classification of canine or feline leukocytes, it is difficult to classify the canine or feline leukocytes unlike human leukocytes.

In FIG. 1, eosinophils are not classified into an independent sub-group distinguished from other leukocytes. In blood examination of pets, especially canine and feline, however, classification of eosinophils by distinguishing them from other leukocytes is very important for diagnosis of allergic diseases and parasitosis, as described above.

Accordingly, the present inventors examined a lysing reagent for classifying canine and feline leukocytes, particularly a lysing reagent capable of classifying eosinophils into an independent sub-group distinguished from other leukocytes. In advancing this examination, the present inventors paid attention to a quaternary ammonium salt contained in the lysing reagent. As a result, they found a lysing reagent capable of classifying canine or feline leukocytes into a first group containing lymphocytes, a second group containing neutrophils and monocytes and a third group containing eosinophils.

The lysing reagent comprises a quaternary ammonium salt lysing erythrocytes and shrinking leukocytes in a blood sample and an aqueous solvent dissolving the quaternary ammonium salt. The concentration of the quaternary ammonium salt is a concentration satisfying the following conditions: The erythrocytes are sufficiently lysed; the leukocytes are shrunk such that the leukocytes can be classified on the basis of their size into 3 sub-groups, that is, a first group containing lymphocytes, a second group containing neutrophils and monocytes and a third group containing eosinophils.

Specifically, the concentration of the quaternary ammonium salt is preferably 1.5 mM or more in order to lyse erythrocytes sufficiently. For classifying leukocytes as described above, the concentration is preferably 20 mM or less, more preferably 14.5 mM or less.

As the quaternary ammonium salt, for example, an alkyl trimethyl ammonium salt having an alkyl group having a carbon number of 10 to 20 is used. The quaternary ammonium salt is preferably an alkyl trimethyl ammonium salt having an alkyl group having a carbon number of 12 to 18. The alkyl group includes a decane group, lauryl group, myristyl group, cetyl group, stearyl group etc.

As the number of carbon atoms in the alkyl group is increased, the power of the alkyl trimethyl ammonium salt to lyse erythrocytes and shrink leukocytes (hereinafter, abbreviated as lysis power) tends to increase. As the number of carbon atoms in the alkyl group is increased, the clouding point of the alkyl trimethyl ammonium salt tends to be lowered. Therefore, when one kind of alkyl trimethyl ammonium salt is used, inferior lysis of erythrocytes may occur, or leukocytes may be shrunk excessively, or precipitation may occur. For more evident classification of the sub-groups of leukocytes, it is preferable to combine a plurality of alkyl trimethyl ammonium salts in order to control the lysis power of the lysing reagent as a whole. Such combination is preferably a combination of an alkyl trimethyl ammonium salt having an alkyl group containing fewer carbon atoms (first alkyl trimethyl ammonium salt) and an alkyl trimethyl ammonium salt having an alkyl group containing more carbon atoms (second alkyl trimethyl ammonium salt). Specifically, the first alkyl trimethyl ammonium salt includes a decane trimethyl ammonium salt and lauryl trimethyl ammonium salt, and the second alkyl trimethyl ammonium salt includes a cetyl trimethyl ammonium salt and stearyl trimethyl ammonium salt. The combination of the two is more preferably a combination of a lauryl trimethyl ammonium salt as the first alkyl trimethyl ammonium salt and a stearyl trimethyl ammonium salt as the second alkyl trimethyl ammonium salt.

When the two are combined, the concentration of the second alkyl trimethyl ammonium salt is preferably lower than the concentration of the first alkyl trimethyl ammonium salt. Specifically, the concentration of the lauryl trimethyl ammonium salt is preferably 20 mM or less, more preferably 8 to 20 mM. The concentration of the stearyl trimethyl ammonium salt is preferably 2 mM or less, more preferably 0.4 to 2 mM, most preferably 1 to 2 mM.

As the second alkyl trimethyl ammonium salt, a cetyl trimethyl ammonium salt can be used in place of the stearyl trimethyl ammonium salt. Because the lysis power of the alkyl trimethyl ammonium salt is increased as the number of carbon atoms in the alkyl group is increased, the lysis power of the cetyl trimethyl ammonium salt is lower than that of the stearyl trimethyl ammonium salt. It follows that when the cetyl trimethyl ammonium salt is used, the concentration thereof is preferably 3 mM or less, more preferably 1.5 to 3 mM.

A small amount of a myristyl trimethyl ammonium salt may further be combined with the combination described above. By doing so, the resulting lysing reagent can exhibit more stable lysis power on various samples. The concentration of the myristyl trimethyl ammonium salt is preferably 0.5 to 1.3 mM, more preferably 0.6 to 0.8 mM.

Further, a small amount of an alkyl dimethyl ethyl ammonium salt may be added to the lysing reagent. By doing so, a lysed erythrocyte can be shrunk more effectively. The alkyl dimethyl ethyl ammonium salt includes, for example, a cetyl dimethyl ethyl ammonium salt, and its concentration is preferably 0.4 to 1.1 mM, more preferably 0.5 to 0.8 mM.

Further addition of a nonionic surfactant having a Hydrophilic-Lipophilic-Balance (HLB) value of 17 to 20 to the lysing reagent is effective in obtaining a highly accurate particle size distribution by shrinking lysed erythrocytes and stabilizing shrunk leukocytes. Examples of the nonionic surfactant include polyoxyethylene cetyl ether, polyoxyethylene lauryl ether, polyoxyethylene oleyl ether, polyoxyethylene behenyl ether, polyoxyethylene nonyl phenyl ether and polyoxyethylene octyl phenyl ether, and the number of polyoxyethylene chains therein is preferably 20 to 100. The concentration of the nonionic surfactant is preferably 0.05 to 0.5 w/v %, more preferably 0.1 to 0.2 w/v %.

As a hemoglobin stabilizer, 5 to 30 mM nitrite salt, 5 to 30 mM nitrate salt, 5 to 50 mM alkyl trimethyl ammonium salt having an alkyl group having a carbon number 1 to 8 or 5 to 50 mM tetraalkyl ammonium salt having an alkyl group having a carbon number of 1 to 8 may be added to the lysing reagent. The alkyl group includes a methyl group, ethyl group, propyl group, butyl group, pentyl group, hexyl group, heptyl group and octyl group. Examples of the alkyl trimethyl ammonium salt and tetraalkyl ammonium salt include an ethyl trimethyl ammonium salt, octyl trimethyl ammonium salt, tetraethyl ammonium salt, tetrabutyl ammonium salt etc.

The above-mentioned aqueous solvent dissolving the quaternary salt includes water and buffers.

The osmotic pressure of the lysing reagent is kept preferably at 200 to 350 mmol/kg. The osmotic pressure can be regulated with an alkali metal salt such as sodium chloride or potassium chloride.

The lysing reagent is kept preferably at pH 4 to 9. For pH regulation, known buffers can be used.

By using the lysing reagent described above, canine and feline leukocytes can be classified and counted. In the method therefor, a canine or feline blood sample is first mixed with the lysing reagent to prepare a measurement sample. In this step, erythrocytes in this sample are lysed. On the other hand, leukocytes are shrunk to remain. Lysis of erythrocytes and shrinkage of leukocytes can occur simultaneously by regulating the type and concentration of the quaternary ammonium salt(s) contained in the lysing reagent, or can occur separately such that erythrocytes are first lysed and leukocytes are then shrunk or vice versa. It is not evident how leukocytes are shrunk, but it is estimated that by mixing a blood sample with the lysing reagent, the cell membrane of leukocyte in the sample is damaged thereby eluting the cytoplasm or baring the nucleus, through which the leukocytes are eventually shrunk. The size of the shrunk leukocytes varies depending on sub-group, so that depending on the size, the leukocytes can be classified into a sub-group and can be counted. Specifically, a lysing reagent is used which shrinks leukocytes such that the size of the leukocytes after shrinkage is made different among lymphocytes, neutrophils and monocytes, and eosinophils, whereby the leukocytes can be classified finally into a first group containing lymphocytes, a second group containing neutrophils and monocytes and a third group containing eosinophils. A measurement sample may be prepared by diluting the blood sample with a diluent, then adding the lysing reagent to the diluted blood sample, and reacting the mixture (for 11 to 15 seconds, for example). As the diluent, physiological saline or a buffer, pH 4 to 9, having an osmotic pressure of 200 to 350 mmol/kg can be used.

After the measurement sample is prepared as described above, data correlated with the size of leukocytes in the measurement sample are measured. On the basis of the measured data, the leukocytes are classified into a first group containing lymphocytes, a second group containing neutrophils and monocytes and a third group containing eosinophils. For example, when an electric resistance method is used in measurement, electric resistance can be mentioned as data correlated with the size of leukocytes. Specifically, the prepared measurement sample is sent to a detector in an electric resistance system in a measuring instrument. In the electric resistance method, the detector is provided with a pore, and both sides of the pore are provided with electrodes, respectively. Direct current is applied across the electrodes, and when a blood corpuscle is passed through the pore, the electric resistance varies in proportion to the volume of the blood corpuscle. This change in electric resistance is detected as a pulse signal, and a signal having pulse height higher than a predetermined level is counted as leukocyte. By converting the pulse height into volume and determining the frequency with which each pulse height is detected, the particle size distribution can be determined. In the determined particle size distribution, there appears a first group containing lymphocytes, a second group containing neutrophils and monocytes and a third group containing eosinophils.

An optical method can also be used in measurement. In this case, the data correlated with the size of leukocytes includes forward scattered light. Specifically, a prepared measurement sample is sent to a detector in a measurement instrument. In the optical method, the detector is irradiated with light, and when a blood corpuscle is passed through the detector, forward scattered light corresponding to the size of the blood corpuscle is detected. On the basis of the intensity of this forward scattered light, the particle size distribution is determined, and leukocytes can be classified into a first group containing lymphocytes, a second group containing neutrophils and monocytes and a third group containing eosinophils.

The correspondence between each sub-group appearing on the particle size distribution and each sub-group of leukocytes can be confirmed by measuring a sample of each sub-group (for example, a sample of separated lymphocytes) separated from a blood sample, and determining the position of the sample in the particle size distribution. Alternatively, the correspondence between each sub-group on the particle size distribution and each sub-group of leukocytes can be confirmed by preparing a smear of a blood sample and comparing data on leukocytes in the smear classified by the visual examination, with data on leukocytes measured by the method of using the lysing reagent described above. Further, a threshold value for dividing the respective sub-groups on the particle size distribution can be established in the position where the difference in the both data becomes minimum. Alternatively, a variable threshold value can be established wherein a valley of particle-size distribution is detected for each sample and the position of the valley is assumed as the threshold value.

By the method of classifying leukocytes with the lysing reagent described above, canine and feline leukocytes can be classified, on the basis of their size, into small leukocytes, middle leukocytes and large leukocytes. The small leukocytes contain lymphocytes, the middle leukocytes contain neutrophils and monocytes, and the large leukocytes contain eosinophils. Because the frequency with which basophils appear in blood is very low, which group basophils belong to is hardly specified, but it is estimated that basophils belong to the middle leukocytes.

The concentration of hemoglobin can be measured by measuring the absorbance of the above prepared measurement sample in the vicinity of 555 nm.

Hereinafter, measurement examples (Example 2 and Example 3) wherein canine and feline blood samples were measured with the lysing reagents described above are described in detail. In Example 2 and Example 3, a blood sample from dog was used as the canine blood sample, and a blood sample from a cat was used as a feline blood sample.

EXAMPLE 2

Lysing reagents 2 to 6 having the same composition as in the lysing reagent 1 except for the concentrations and combination of the quaternary ammonium salts were prepared, and each lysing reagent was used to measure dog and cat blood samples. The quaternary ammonium salts used are as follows:

Alkyl trimethyl ammonium salts
Decane trimethyl ammonium bromide (DTAB): number of carbon atoms in the alkyl group, 10
Lauryl trimethyl ammonium chloride (LTAC): number of carbon atoms in the alkyl group, 12
Myristyl trimethyl ammonium bromide (MTAB): number of carbon atoms in the alkyl group, 14
Stearyl trimethyl ammonium chloride (STAC): number of carbon atoms in the alkyl group, 18
Alkyl dimethyl ethyl ammonium salt
Cetyl dimethyl ethyl ammonium bromide (CDMEB): number of carbon atoms in the alkyl group, 16

The concentrations and combination of the quaternary ammonium salts in the lysing reagents 2 to 6 are as shown in Table 1.

TABLE 1

| | Alkyl trimethyl ammonium salt (mM) | | | | Alkyl dimethyl ethyl ammonium salt (mM) | |
|---|---|---|---|---|---|---|
| | DTAB (C = 10) | LTAC (C = 12) | MTAB (C = 14) | STAC (C = 18) | CDMEB (C = 16) | Total concentration (mM) |
| Lysing reagent 2 | 0 | 18 | 0 | 1.44 | 0 | 19.44 |
| Lysing reagent 3 | 0 | 15 | 0 | 1.2 | 0 | 16.2 |
| Lysing reagent 4 | 0 | 15 | 1.2 | 0.48 | 1.06 | 17.74 |
| Lysing reagent 5 | 12 | 0 | 0.6 | 1.2 | 0.53 | 14.33 |
| Lysing reagent 6 | 0 | 9 | 0.6 | 1.44 | 0.53 | 11.57 |

Using the lysing reagents 2 to 6 shown in Table 1, dog blood samples were measured with an automatic hemocytometer pocH-100iV (Sysmex Corporation). The measurement method was the same as in Example 1. In the same manner as in Example 1, smears were prepared from the blood samples used in measurement, and then subjected to May-Grünwald-Giemsa staining, and the leukocytes were visually classified and counted.

Figure 4:
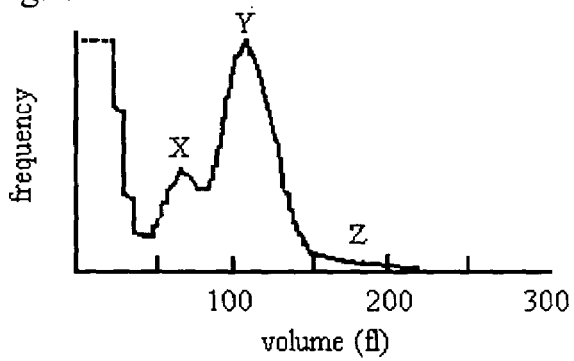
FIG. 4 shows the particle size distribution obtained by measuring a dog blood sample with a lysing reagent 2 in Measurement Example 2.
Figure 5:
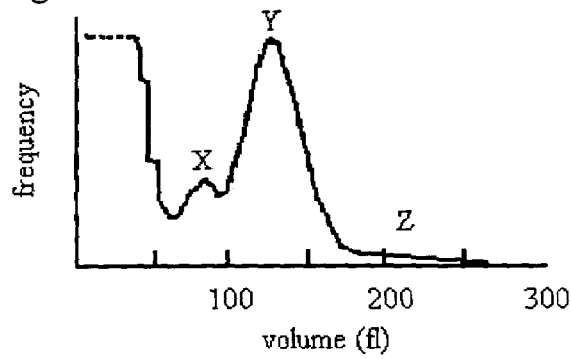
FIG. 5 shows the particle size distribution obtained by measuring a dog blood sample with a lysing reagent 3 in Measurement Example 2.
Figure 6:
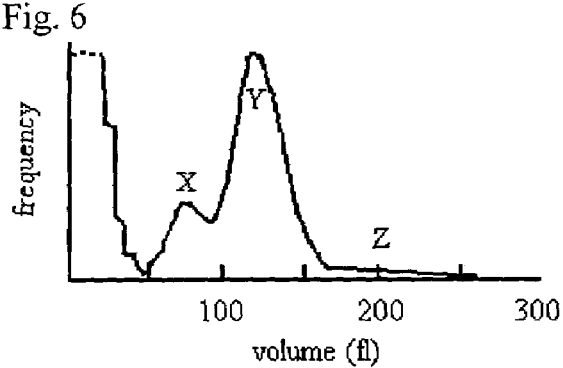
FIG. 6 shows the particle size distribution obtained by measuring a dog blood sample with a lysing reagent 4 in Measurement Example 2.
Figure 7:
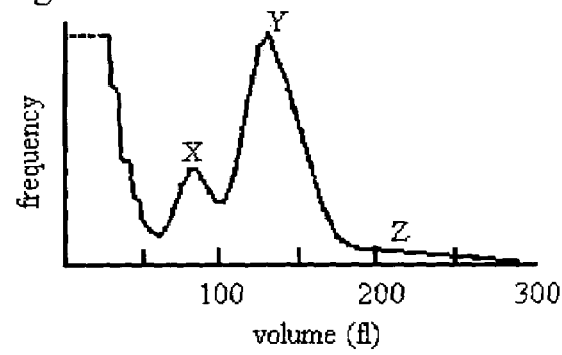
FIG. 7 shows the particle size distribution obtained by measuring a dog blood sample with a lysing reagent 5 in Measurement Example 2.
Figure 8:
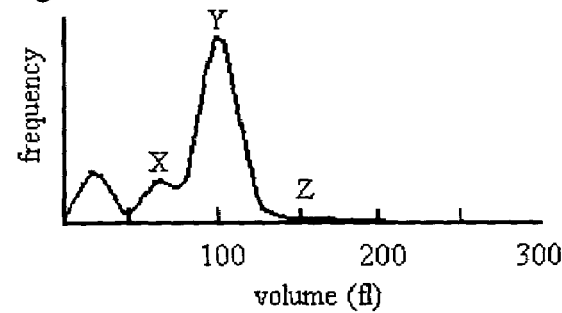
FIG. 8 shows the particle size distribution obtained by measuring a dog blood sample with a lysing reagent 6 in Measurement Example 2.

FIG. 4 shows the particle size distribution obtained by measuring a dog blood sample with the lysing reagent 2. FIG. 5 shows the particle size distribution obtained by measuring a dog blood sample with the lysing reagent 3. FIG. 6 shows the particle size distribution obtained by measuring a dog blood sample with the lysing reagent 4. FIG. 7 shows the particle size distribution obtained by measuring a dog blood sample with the lysing reagent 5. FIG. 8 shows the particle size distribution obtained by measuring a dogblood sample with the lysing reagent 6.

In any of the particle-size distributions in FIGS. 4 to 8, three sub-groups of leukocytes (X, Y and Z) appeared. Comparison thereof with data classified by the visual examination revealed that the X is a group containing lymphocytes, the Y is a group containing neutrophils and monocytes, and the Z is a group containing eosinophils. When data on the respective sub-groups on the particle-size distribution are compared with data on the respective sub-groups obtained by the visual examination, high correlation was obtained particularly in FIGS. 7 and 8.

From the forgoing, it was found that by using the lysing reagents 2 to 6, canine leukocytes can be classified into 3 sub-groups, that is, a group containing lymphocytes, a group containing neutrophils and monocytes, and a group containing eosinophils. It was also found that by using the lysing reagents 5 and 6, leukocytes can be classified more accurately.

Figure 9:
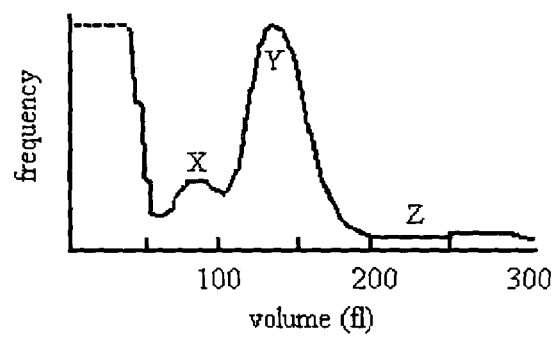
FIG. 9 shows the particle size distribution obtained by measuring a cat blood sample with a lysing reagent 5 in Measurement Example 2.
Figure 10:
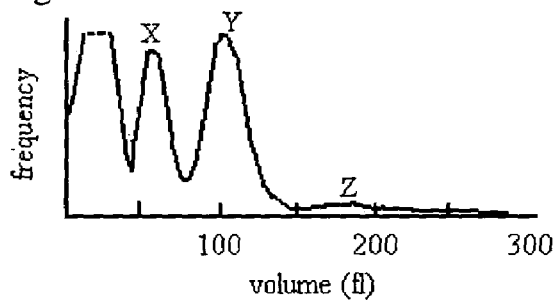
FIG. 10 shows the particle size distribution obtained by measuring a cat blood sample with a lysing reagent 6 in Measurement Example 2.

Using the lysing reagents 5 and 6, cat blood samples were then measured in the same manner as for the dog blood samples. FIG. 9 shows the particle size distribution obtained by measuring a cat blood sample with the lysing reagent 5. FIG. 10 shows the particle size distribution obtained by measuring a cat blood sample with the lysing reagent 6.

In any of the particle-size distributions in FIGS. 9 and 10, three sub-groups of leukocytes (X, Y and Z) appeared. Comparison thereof with data classified by the visual examination revealed that the X is a group containing lymphocytes, the Y is a group containing neutrophils and monocytes, and the Z is a group containing eosinophils.

From the forgoing, it was found that by using the lysing reagents 5 and 6, feline leukocytes similar to the canine leukocytes can be classified into 3 sub-groups, that is, a group containing lymphocytes, a group containing neutrophils and monocytes and a group containing eosinophils.

EXAMPLE 3

Lysing reagent 7 having the following composition containing a nonionic surfactant was used to measure dog and cat blood samples. The nonionic surfactant contained in the lysing reagent 7 is Emulsit 9 (polyoxyethylene nonyl phenyl ether) that is a nonionic surfactant having an HLB of 17 to 20.

| Lysing reagent 7 | |
|---|---|
| Cation-AB (Containing 23% stearyl trimethyl ammonium chloride, manufactured by Nippon Oil & Fats Co., Ltd.) | 2.16 g |
| Lauryl trimethyl ammonium chloride | 2.39 g |
| Cetyl dimethyl ethyl ammonium bromide | 0.2 g |
| Myristyl trimethyl ammonium bromide | 0.2 g |
| Emulsit 9 (Polyoxyethylene nonyl phenyl ether, manufactured by Dai-ichi Kogyo Seiyaku Co., Ltd.) | 1.0 g |
| Sodium chloride | 4.13 g |
| Succinic acid | 3.0 g |
| EDTA-2K.2H$_2$O | 2.5 g |
| Sodium hydroxide | 1.55 g |
| Sodium nitrite | 0.69 g |
| Purified water | 1 L | pH 5.3, osmotic pressure of 280 mmol/kg

The lysing reagent 7 contains, as quaternary ammonium salts, 1.43 mM stearyl trimethyl ammonium chloride, 9 mM lauryl trimethyl ammonium chloride, 0.53 mM cetyl dimethyl ethyl ammonium bromide and 0.6 mM myristyl trimethyl ammonium bromide. Using the lysing reagent 7, 111 dog blood samples and 37 cat blood samples were measured with an automatic hemocytometer pocH-100iV (Cysmex Corporation). The measurement method was the same as in Example 1. In the same manner as in Example 1, smears were prepared from the blood samples used in measurement, and then subjected to May-Grünwald-Giemsa staining, and the leukocytes were visually classified and counted.

<Dog Blood Sample>

Figure 11:
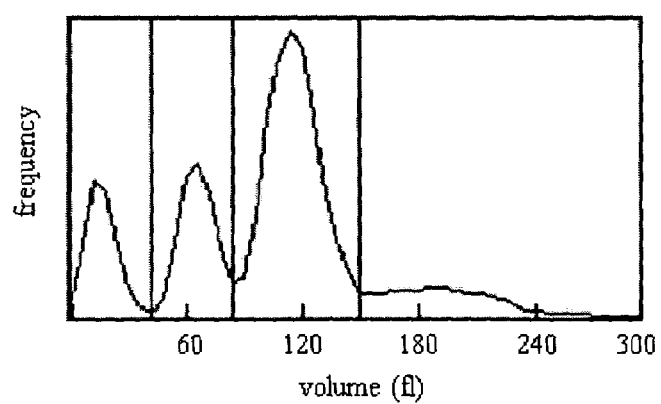
FIG. 11 shows one example of the particle size distribution obtained by measuring a dog blood sample with a lysing reagent 7 in Measurement Example 3.

One example of the particle size distribution measured in dog blood sample is shown in FIG. 11. In FIG. 11, the leftmost group is a group of lysed erythrocytes. Then, the first group (small leukocyte), the second group (middle leukocyte) and the third group (large leukocyte) appear in the order of small to large sizes.

Although the threshold value of each group varies slightly depending on the state of the particle-size distribution obtained, the threshold value was determined as follows: The threshold value between the group of lysed erythrocytes and the first group is in the vicinity of 48 fl; the threshold value between the first and second groups is in the vicinity of 90 fl; the threshold value between the second and third groups is set in the vicinity of 162 fl; and the upper limit is set to 300 fl.

Figure 12:
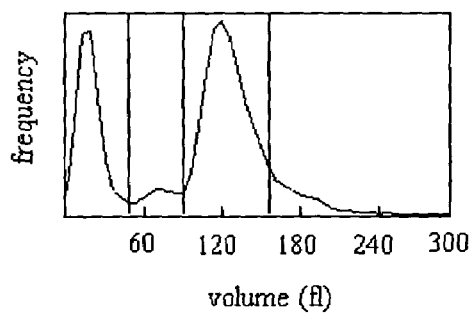
FIG. 12 shows the particle size distribution obtained by measuring a dog blood sample (dog 1) with a lysing reagent 7 in Measurement Example 3.
Figure 13:
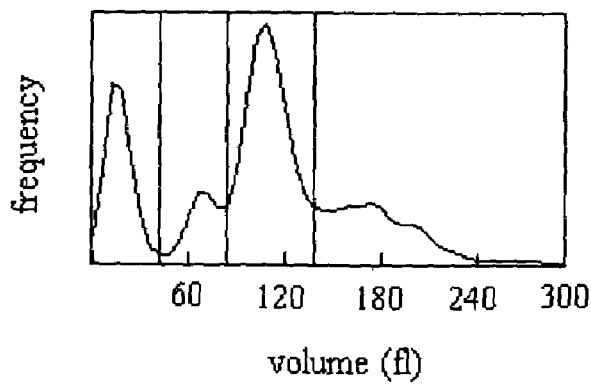
FIG. 13 shows the particle size distribution obtained by measuring a dog blood sample (dog 2) with a lysing reagent 7 in Measurement Example 3.

FIGS. 12 and 13 show the particle-size distributions of 2 samples (dogs 1 and 2) among the dog samples measured. In any of the distributions, similar to the distribution in FIG. 11, a group of lysed erythrocytes appeared in the leftmost position, and then the first group (small leukocyte), the second group (middle leukocyte) and the third group (large leukocyte) appeared in the order of small to large sizes.

Then, the data on the small, middle and large leukocytes appearing in the particle-size distributions in FIGS. 12 and 13 were compared with data obtained by classifying and counting the leukocytes by the visual examination. The results are shown in Table 2.

Eosinophil ratio (%) is the ratio of the number of eosinophils to the number of total leukocytes.

From Table 2, it was found that the SCR value is close to the value of lymphocyte ratio. It was also found that the MCR is close to the total sum of monocyte ratio (%) and neutrophil ratio (%). It was further found that the LCR value is close to the value of eosinophil ratio.

Figure 14:
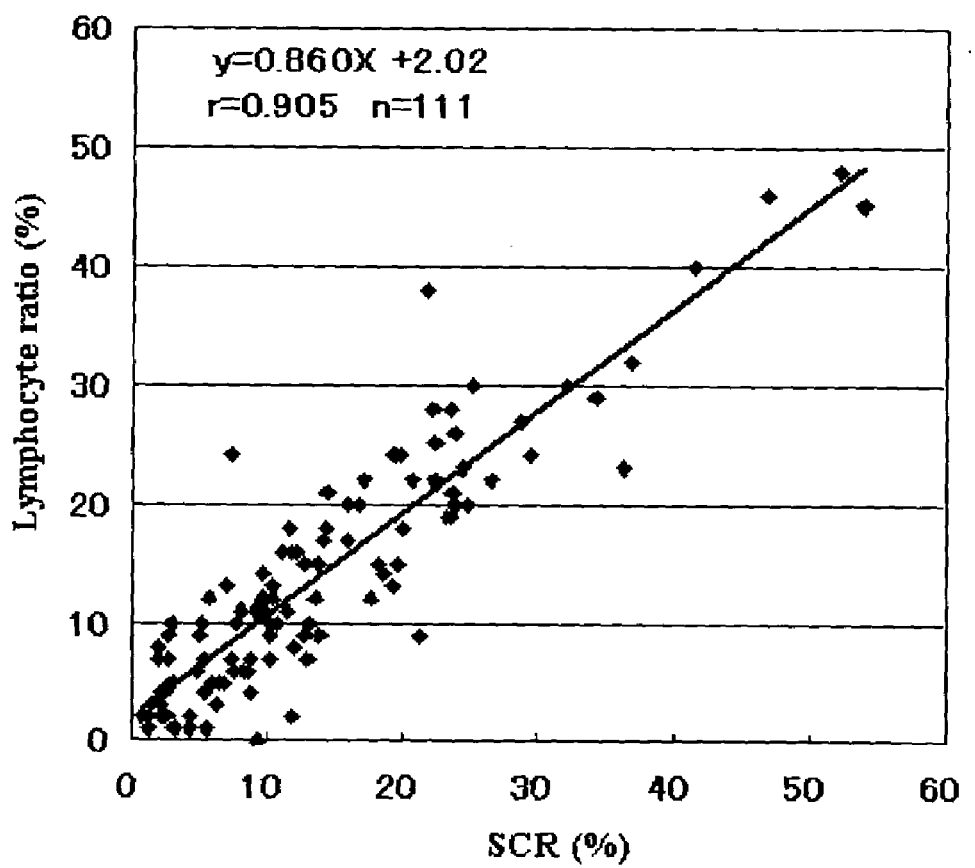
FIG. 14 shows the correlation of small cell ratio (SCR) obtained with a lysing reagent 7 with lymphocyte ratio obtained by a visual examination for a dog blood sample in Measurement Example 3.
Figure 15:
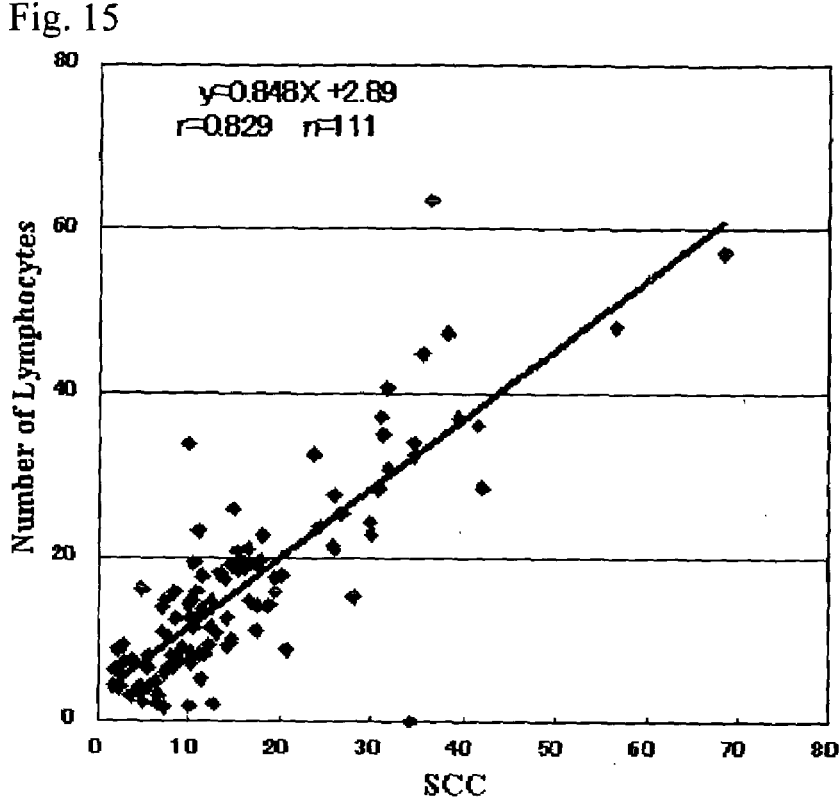
FIG. 15 shows the correlation of small cell count (SCC) obtained with a lysing reagent 7 with lymphocyte count obtained by a visual examination for a dog blood sample in Measurement Example 3.

Thus, the correlation of SCR with lymphocyte ratio obtained by the visual examination on dog blood samples (111 samples) was examined, and as a result, the correlation therebetween was better (FIG. 14). Accordingly, it is found that the small leukocyte group contains lymphocytes. The correlation of the number of small leukocytes (small cell count (SCC)) with the number of lymphocytes obtained by the visual examination was also better (FIG. 15).

Figure 16:
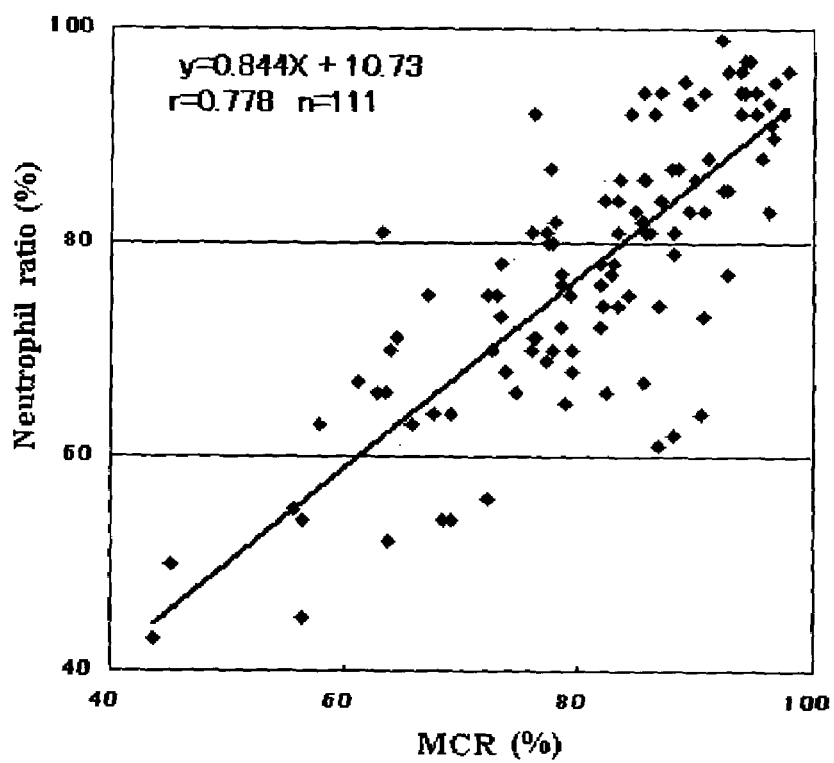
FIG. 16 shows the correlation of middle cell ratio (MCR) obtained with a lysing reagent 7 with neutrophil ratio obtained by a visual examination for a dog blood sample in Measurement Example 3.
Figure 17:
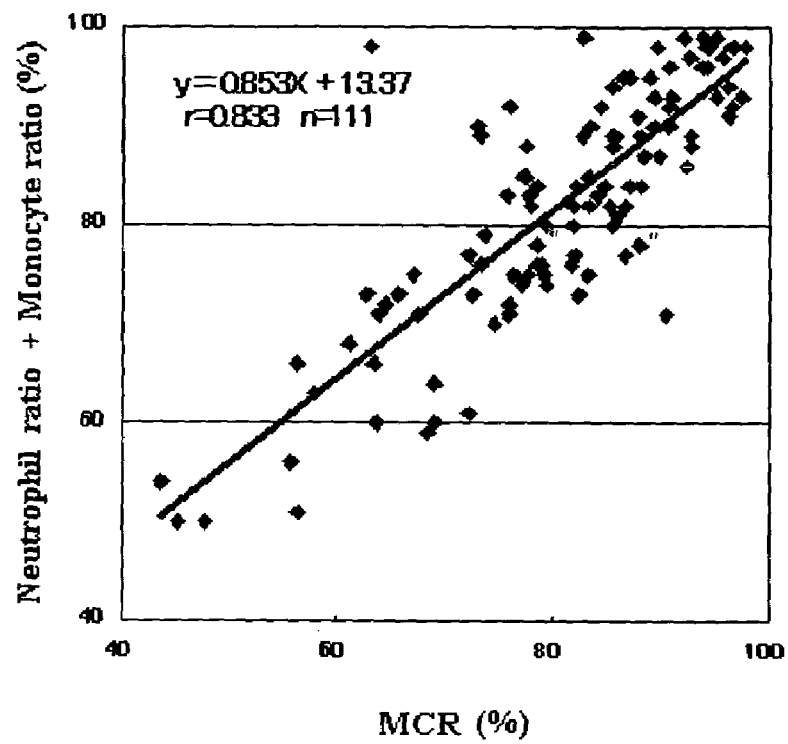
FIG. 17 shows the correlation of middle cell ratio (MCR) obtained with a lysing reagent 7 with neutrophil ratio+monocyte ratio obtained by a visual examination for a dog blood sample in Measurement Example 3.
Figure 18:
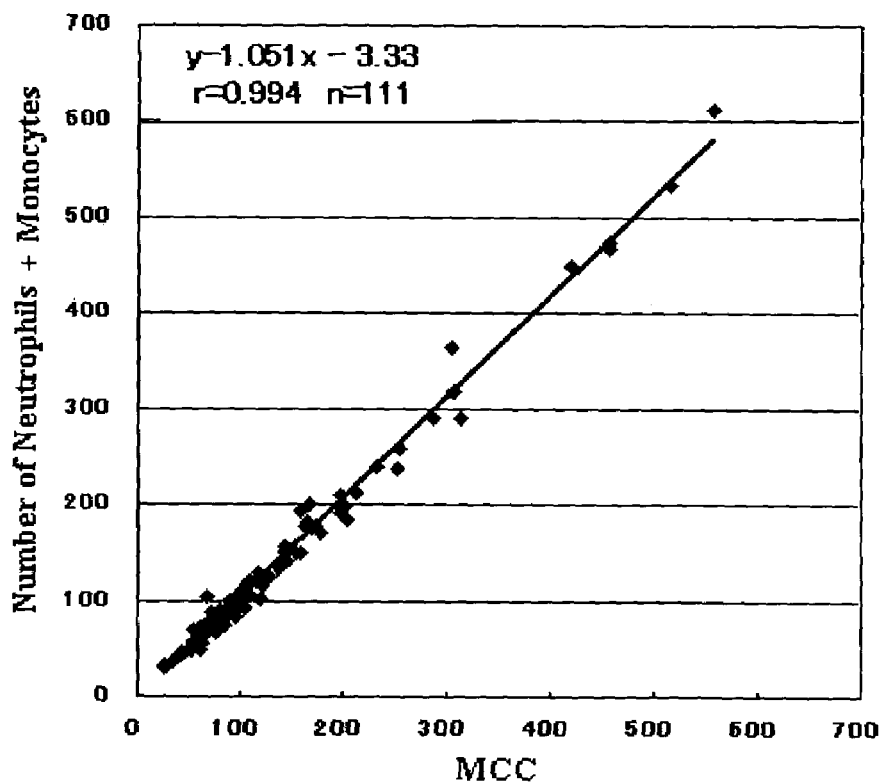
FIG. 18 shows the correlation of middle cell count (MCC) obtained with a lysing reagent 7 with the number of neutrophils+number of monocytes obtained by a visual examination for a dog blood sample in Measurement Example 3.

Then, the correlation of MCR with neutrophil ratio obtained by the visual examination was examined (FIG. 16). Further, the correlation of MCR with neutrophil ratio+monocyte ratio obtained by the visual examination was examined (FIG. 17). The correlation in FIG. 17 was better as compared with FIG. 16. The correlation of the number of middle leukocytes (middle cell count (MCC)) with number of neutrophils+number of monocytes obtained by the visual examination was also better (FIG. 18).

Figure 19:
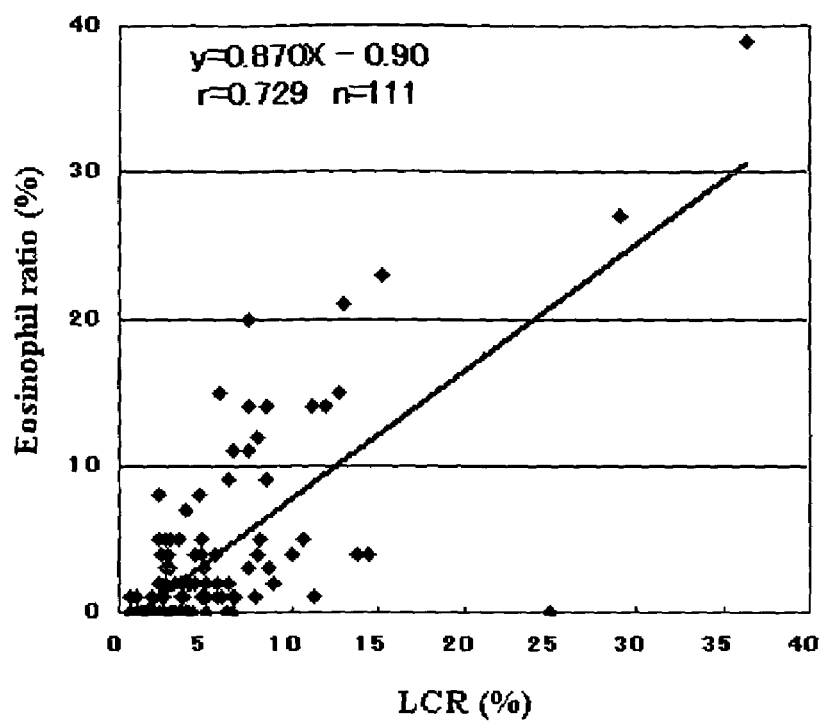
FIG. 19 shows the correlation of large cell ratio (LCR) obtained with a lysing reagent 7 with eosinophil ratio obtained by a visual examination for a dog blood sample in Measurement Example 3.
Figure 20:
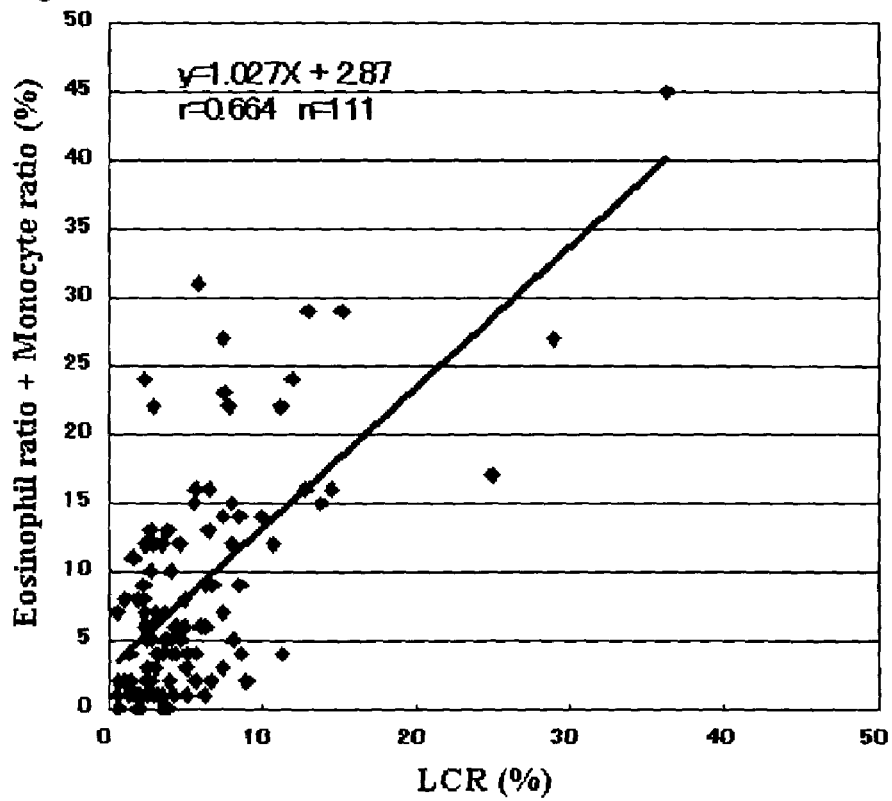
FIG. 20 shows the correlation of large cell ratio (LCR) obtained with a lysing reagent 7 with eosinophil ratio+monocyte ratio obtained by a visual examination for a dog blood sample in Measurement Example 3.
Figure 21:
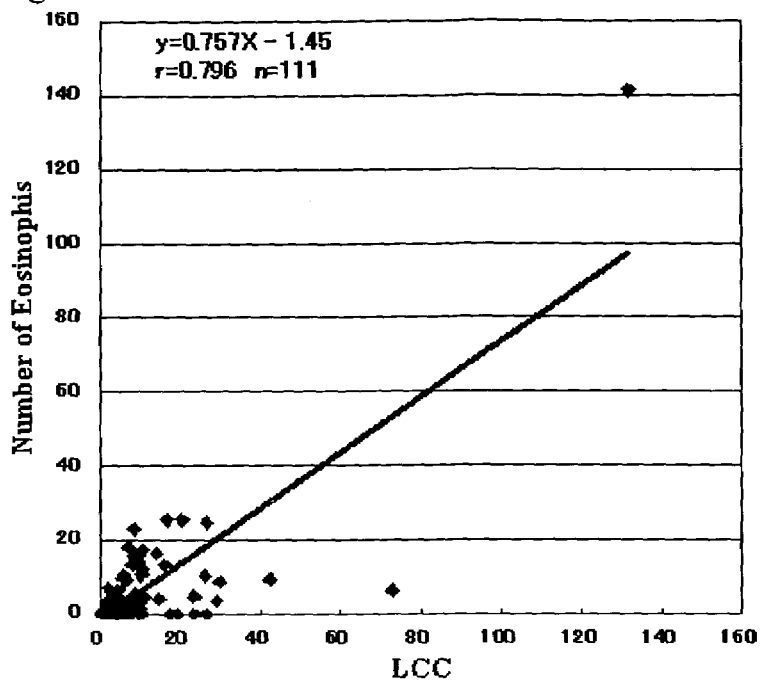
FIG. 21 shows the correlation of large cell count (LCC) obtained with a lysing reagent 7 with the number of eosinophils obtained by a visual examination for a dog blood sample in Measurement Example 3.

Further, the correlation of LCR with eosinophil ratio obtained by the visual examination was examined (FIG. 19). Further, the correlation of LCR with eosinophil ratio+monocyte ratio obtained by the visual examination was examined (FIG. 20). The correlation in FIG. 19 was better as compared with FIG. 20. The correlation of the number of large leukocytes (large cell count (LCC)) with the number of eosinophils obtained by the visual examination was also better (FIG. 21).

In this example, a sample where basophils appeared was not found by the visual examination.

TABLE 2

| | Classification of leukocytes with the lysing reagent 7 | | | Classification of leukocytes by the visual examination | | | |
|---|---|---|---|---|---|---|---|
| | SCR (%) | MCR (%) | LCR (%) | Lymphocyte ratio (%) | Neutrophil ratio (%) | Monocyte ratio (%) | Eosinophil ratio (%) |
| Dog 1 (FIG. 12) | 8.6 | 79.4 | 12.0 | 6 | 70 | 10 | 14 |
| Dog 2 (FIG. 13) | 13.1 | 57.9 | 29 | 10 | 63 | 0 | 27 |

In Table 2, SCR (%), MCR (%) and LCR (%) are values calculated on the basis of data on small leukocytes, middle leukocytes and large leukocytes appearing in the particle-size distributions in FIGS. 12 and 13. SCR (%) is the ratio of the number of small leukocytes to the number of total leukocytes (small cell ratio (SCR)). MCR (%) is the ratio of the number of middle leukocytes to the number of total leukocytes (middle cell ratio (MCR)). LCR (%) is the ratio of the number of large leukocytes to the number of total leukocytes (large cell ratio (LCR)). On the other hand, lymphocyte ratio (%), neutrophil ratio (%), monocytes ratio (%) and eosinophil ratio (%) are values calculated on the basis of data obtained by classifying and counting leukocytes by the visual examination. Lymphocyte ratio (%) is the ratio of the number of lymphocytes to the number of total leukocytes. Neutrophil ratio (%) is the ratio of the number of neutrophils to the number of total leukocytes. Monocyte ratio (%) is the ratio of the number of monocytes to the number of total leukocytes.

From the foregoing, it is found that the group of middle leukocytes contains neutrophils and monocytes, and the group of large leukocytes contains eosinophils.

<Cat Blood Sample>

Figure 22:
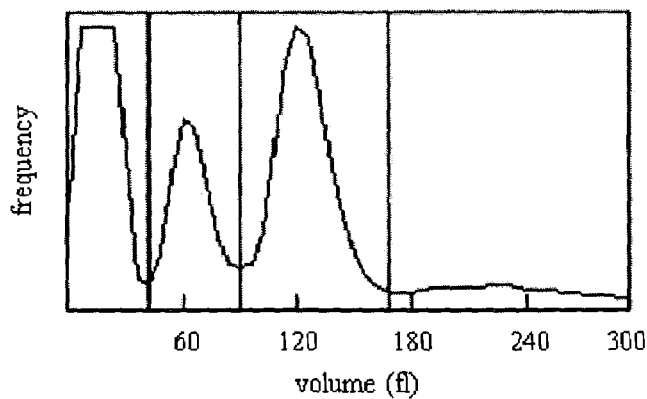
FIG. 22 shows one example of the particle size distribution obtained by measuring a cat blood sample with a lysing reagent 7 in Measurement Example 3.

One example of the particle size distribution measured in cat blood sample is shown in FIG. 22. In FIG. 22, the leftmost group is a group of lysed erythrocytes. Then, the first group (small leukocyte), the second group (middle leukocyte) and the third group (large leukocyte) appeared in the order of small to large sizes.

Although the threshold value of each group varies slightly depending on the state of the particle-size distribution obtained, the threshold value was determined as follows: The threshold value between the group of lysed erythrocytes and the first group is in the vicinity of 48 fl; the threshold value between the first and second groups is in the vicinity of 96 fl; the threshold value between the second and third groups is in the vicinity of 174 fl; and the upper limit is 300 fl.

Figure 23:
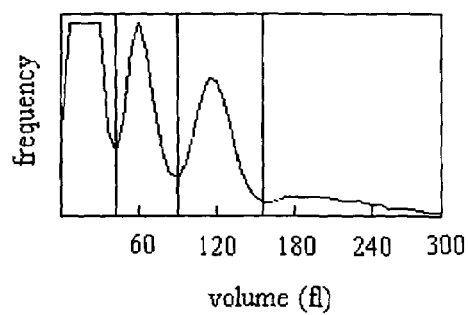
FIG. 23 shows the particle size distribution obtained by measuring a cat blood sample (cat 1) with a lysing reagent 7 in Measurement Example 3.
Figure 24:
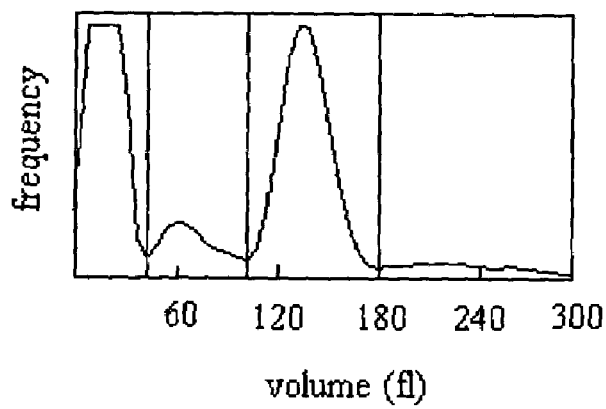
FIG. 24 shows the particle size distribution obtained by measuring a cat blood sample (cat 2) with a lysing reagent 7 in Measurement Example 3.

FIGS. 23 and 24 show the particle-size distributions of 2 samples (cats 1 and 2) among the cat samples measured. In any of the distributions, similar to the distribution in FIG. 22, a group of lysed erythrocytes appeared in the leftmost position, and then the first group (small leukocyte), the second group (middle leukocyte) and the third group (large leukocyte) appeared in the order of small to large sizes.

Then, the data on the small, middle and large leukocytes appearing in the particle-size distributions in FIGS. 23 and 24 were compared with data obtained by classifying and counting the leukocytes by the visual examination. The results are shown in Table 3.

TABLE 3

| | Classification of leukocytes with the lysing reagent 7 | | | Classification of leukocytes by the visual examination | | | |
|---|---|---|---|---|---|---|---|
| | SCR (%) | MCR (%) | LCR (%) | Lymphocyte ratio (%) | Neutrophil ratio (%) | Monocyte ratio (%) | Eosinophil ratio (%) |
| Cat 1 (FIG. 23) | 16.6 | 74.8 | 8.6 | 18 | 67 | 4 | 11 |
| Cat 2 (FIG. 24) | 44.7 | 42.3 | 13.0 | 39 | 40 | 5 | 16 |

In Table 3, SCR (%), MCR (%) and LCR (%) are values calculated on the basis of data on small leukocytes, middle leukocytes and large leukocytes appearing in the particle-size distributions in FIGS. 23 and 24. SCR (%) is the ratio of the number of small leukocytes to the number of total leukocytes (small cell ratio (SCR)). MCR (%) is the ratio of the number of middle leukocytes to the number of total leukocytes (middle cell ratio (MCR)). LCR (%) is the ratio of the number of large leukocytes to the number of total leukocytes (large cell ratio (LCR)). On the other hand, lymphocyte ratio (%), neutrophil ratio (%), monocytes ratio (%) and eosinophil ratio (%) are values calculated on the basis of data obtained by classifying and counting leukocytes by the visual examination. Lymphocyte ratio (%) is the ratio of the number of lymphocytes to the number of total leukocytes. Neutrophil ratio (%) is the ratio of the number of neutrophils to the number of total leukocytes. Monocyte ratio (%) is the ratio of the number of monocytes to the number of total leukocytes. Eosinophil ratio (%) is the ratio of the number of eosinophils to the number of total leukocytes.

From Table 3, it was found that the SCR value is close to the value of lymphocyte ratio. It was also found that the MCR is close to the total sum of monocyte ratio (%) and neutrophil ratio (%). It was further found that the LCR value is close to the value of eosinophil ratio.

Figure 25:
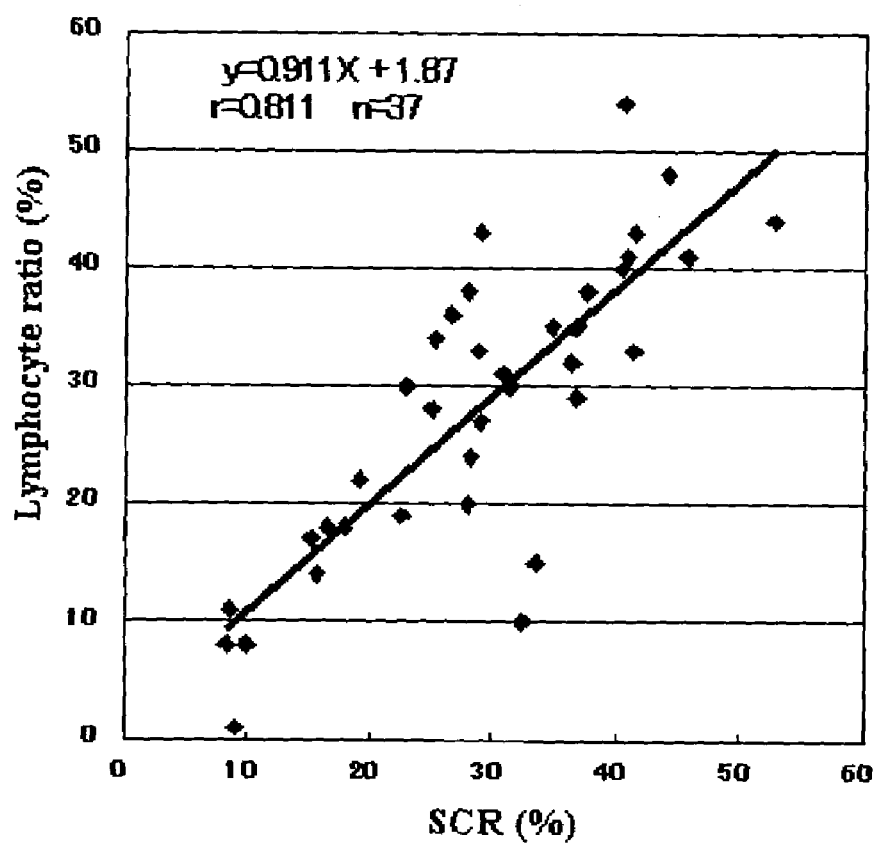
FIG. 25 shows the correlation of small cell ratio (SCR) obtained with a lysing reagent 7 with lymphocyte ratio obtained by a visual examination for a cat blood sample in Measurement Example 3.
Figure 26:
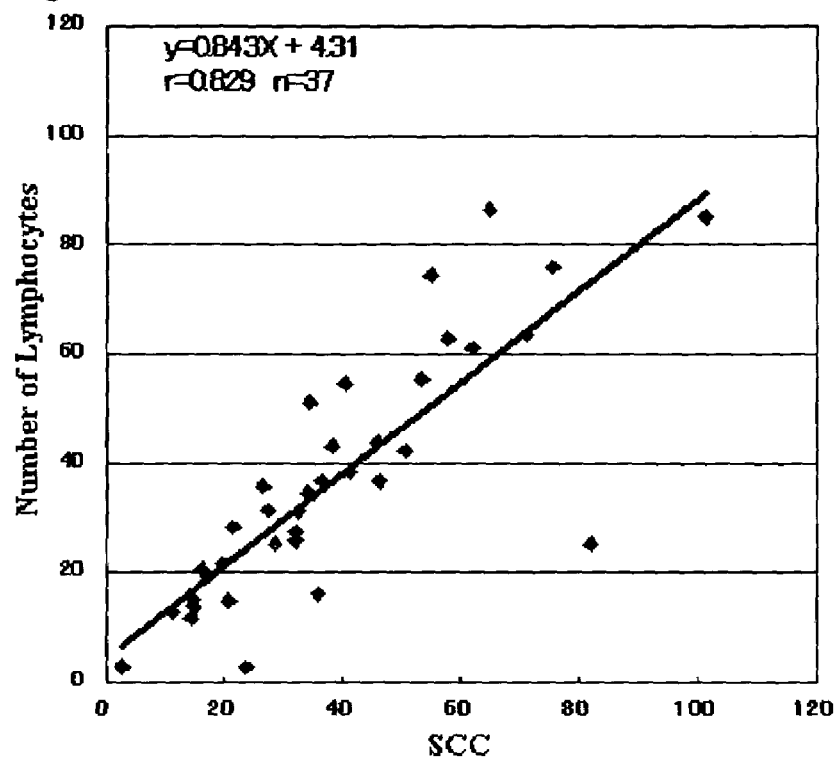
FIG. 26 shows the correlation of small cell count (SCC) obtained with a lysing reagent 7 with the number of lymphocytes obtained by a visual examination for a cat blood sample in Measurement Example 3.

Thus, the correlation of SCR with lymphocyte ratio obtained on cat blood samples (37 samples) by the visual examination was examined, and as a result, the correlation therebetween was better (FIG. 25). Accordingly, it is found that the small leukocyte group contains lymphocytes. The correlation of the number of small leukocytes (small cell count (SCC)) with the number of lymphocytes obtained by the visual examination was also better (FIG. 26).

Figure 27:
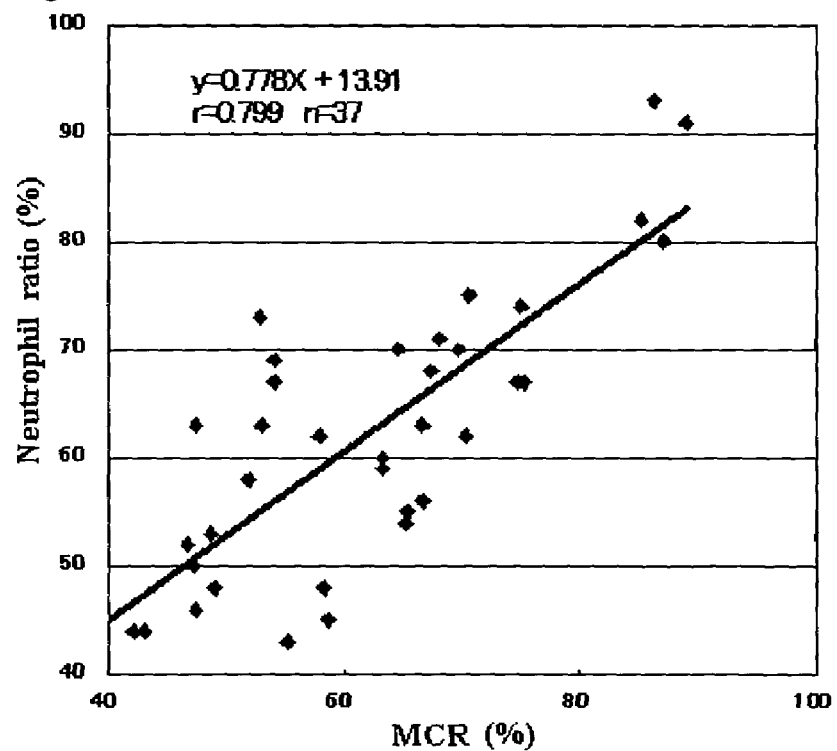
FIG. 27 shows the correlation of middle cell ratio (MCR) obtained with a lysing reagent 7 with neutrophil ratio obtained by a visual examination for a cat blood sample in Measurement Example 3.
Figure 28:
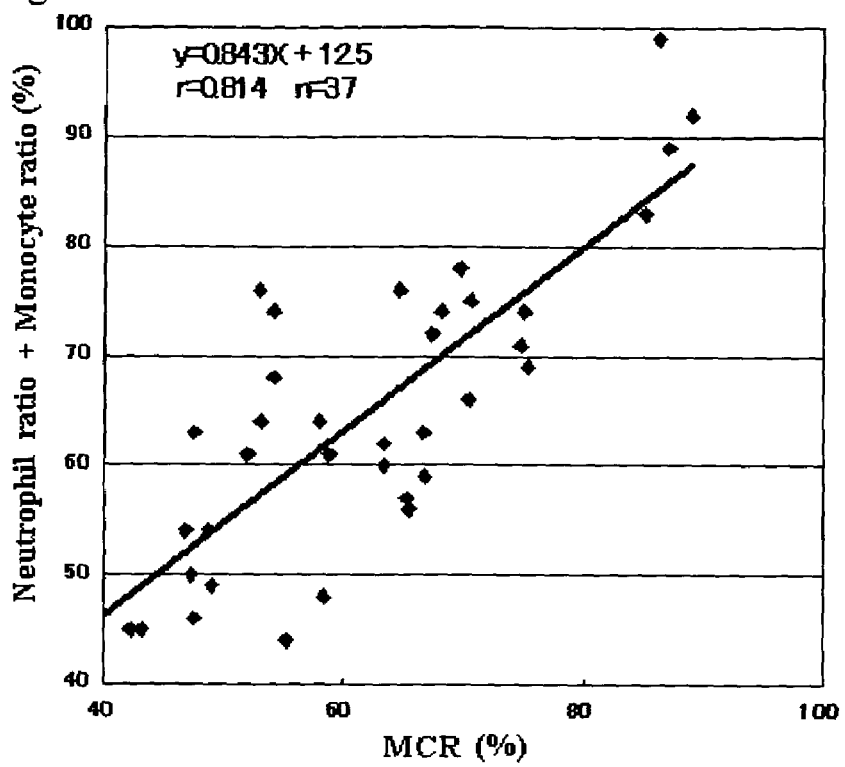
FIG. 28 shows the correlation of middle cell ratio (MCR) obtained with a lysing reagent 7 with neutrophil ratio+monocyte ratio obtained by a visual examination for a cat blood sample in Measurement Example 3.
Figure 29:
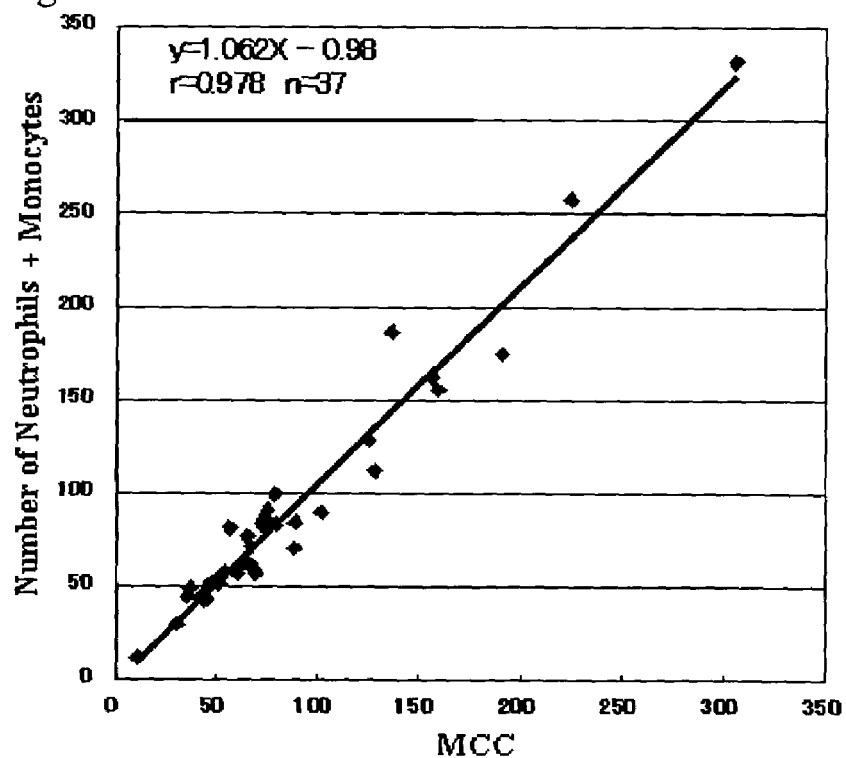
FIG. 29 shows the correlation of middle cell count (MCC) obtained with a lysing reagent 7 with the number of neutrophils+number of monocytes obtained by a visual examination for a cat blood sample in Measurement Example 3.

Then, the correlation of MCR with neutrophil ratio obtained by the visual examination was examined (FIG. 27). Further, the correlation of MCR with neutrophil ratio+monocyte ratio obtained by the visual examination was examined (FIG. 28). The correlation in FIG. 28 was better as compared with FIG. 27. The correlation of the number of middle leukocytes (middle cell count (MCC)) with number of neutrophils+number of monocytes obtained by the visual examination was also better (FIG. 29).

Figure 30:
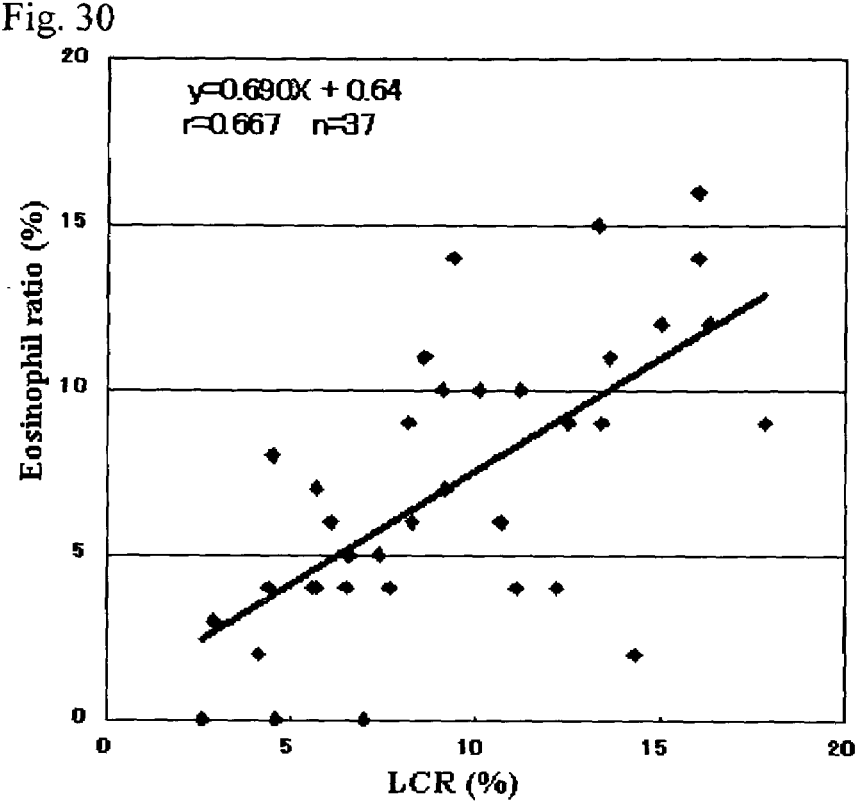
FIG. 30 shows the correlation of large cell ratio (LCR) obtained with a lysing reagent 7 with eosinophil ratio obtained by a visual examination for a cat blood sample in Measurement Example 3.
Figure 31:
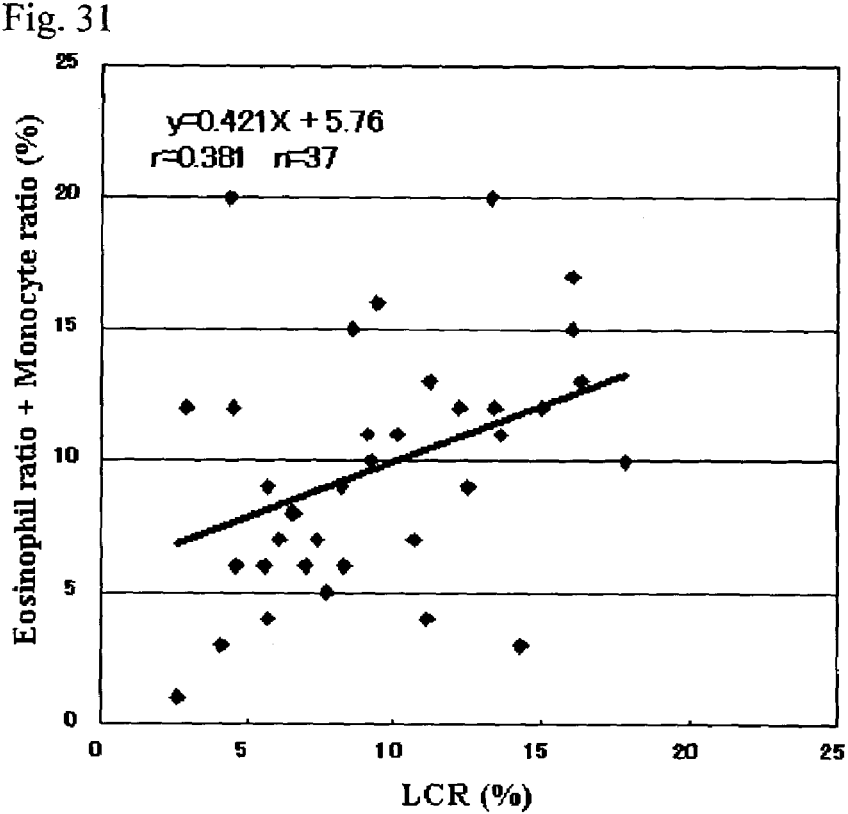
FIG. 31 shows the correlation of large cell ratio (LCR) obtained with a lysing reagent 7 with eosinophil ratio+monocyte ratio obtained by a visual examination for a cat blood sample in Measurement Example 3.
Figure 32:
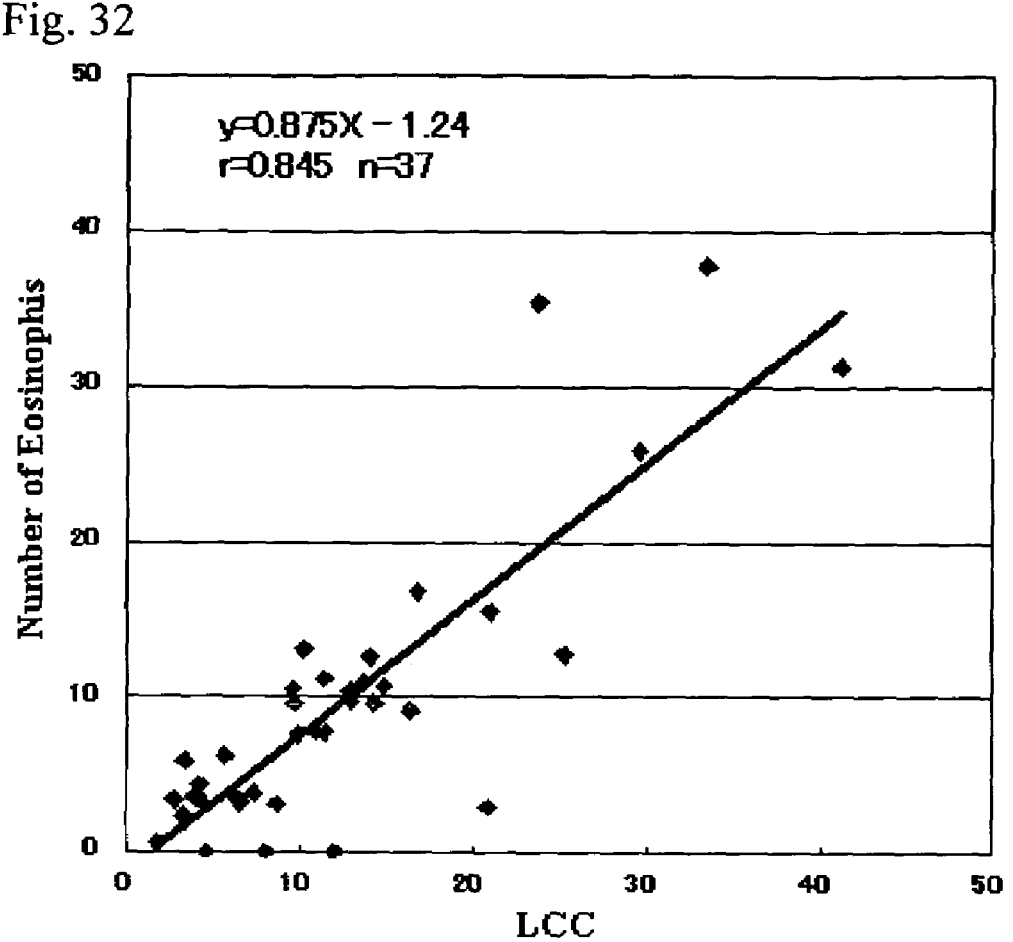
FIG. 32 shows the correlation of large cell count (LCC) obtained with a lysing reagent 7 with the number of eosinophils obtained by a visual examination for a cat blood sample in Measurement Example 3.

Further, the correlation of LCR with neutrophil ratio obtained by the visual examination was examined (FIG. 30). Further, the correlation of LCR with eosinophil ratio+monocyte ratio obtained by the visual examination was examined (FIG. 31). The correlation in FIG. 30 was better as compared with FIG. 31. The correlation of the number of large leukocytes (large cell count (LCC)) with the number of eosinophils obtained by the visual examination was also better (FIG. 32).

In this example, a sample where basophils appeared was not found by the visual examination.

From the foregoing, it is found that the group of middle leukocytes contains neutrophils and monocytes, and the group of large leukocytes contains eosinophils.

<Hemoglobin Concentration>

When dog blood samples and cat blood samples were measured for their hemoglobin concentrations with pocH-100iV by using the lysing reagent 7 and a conventional product Stomatorizer-WH (Sysmex Corporation), the correlation therebetween was better. It was thus confirmed that the hemoglobin concentration can be measured by the lysing reagent 7.

The method and reagent for classifying canine and feline leukocytes can give results of blood examination more accurately in more detail than conventional, thus enabling more suitable diagnosis and monitoring of therapy for canine and feline diseases including parasitosis and allergic diseases.

What is claimed is:

1. A method for classifying leukocytes in canine or feline blood, comprising the steps of:
   preparing a measurement sample by mixing a canine or feline blood sample with a lysing reagent, the lysing reagent comprising a first alkyl trimethyl ammonium salt having an alkyl group having a carbon number of 10 to 12 and a second alkyl trimethyl ammonium salt having an alkyl group having a carbon number of 16 to 18, wherein erythrocytes are lysed and leukocytes are shrunk in the measurement sample;
   measuring data correlated with the size of leukocytes in the measurement sample; and
   classifying the leukocytes, on the basis of the measured data, into a first group consisting essentially of lymphocytes, a second group consisting essentially of neutrophils and monocytes and a third group consisting essentially of eosinophils.

2. The method according to claim 1, wherein the data correlated with the size of leukocytes in the measurement sample is electric resistance measured by an electric resistance method.

3. The method according to claim 1, wherein in the step of preparing the measurement sample, leukocytes are shrunk such that lymphocytes, neutrophils and monocytes, and eosinophil appear in the order of small to large sizes after shrinkage.

4. The method according to claim 1, wherein the first, second and third groups appear in the order of small to large sizes based on the data correlated with the size of leukocytes.

5. The method according to claim 1, wherein the concentration of the alkyl trimethyl ammonium salts is a concentration satisfying the following conditions: (1) erythrocytes are sufficiently lysed, and (2) leukocytes are shrunk such that the leukocytes can be classified, on the basis of their size, into the first, second and third groups.

6. The method according to claim 1, wherein the concentration of the alkyl trimethyl ammonium salts is 1.5 mM to 20 mM.

7. The method according to claim 1, wherein
the first alkyl trimethyl ammonium salt is selected from a lauryl trimethyl ammonium salt, and
the second alkyl trimethyl ammonium salt is selected from the group consisting of a stearyl trimethyl ammonium salt and a cetyl trimethyl ammonium salt.

8. The method according to claim 7, wherein the concentration of the lauryl trimethyl ammonium salt is 8 to 20 mM, the concentration of the stearyl trimethyl ammonium salt is 0.4 to 2 mM, and the concentration of the cetyl trimethyl ammonium salt is 1.5 to 3 mM.

9. The method according to claim 1, wherein the lysing reagent further comprises a myristyl trimethyl ammonium salt.

10. The method according to claim 1, wherein the lysing reagent further comprises an alkyl dimethyl ethyl ammonium salt.

11. The method according to claim 1, wherein the lysing reagent further comprises a nonionic surfactant having a Hydrophilic-Lipophilic-Balance value of 17 to 20.

12. The method according to claim 1, wherein the pH value of the lysing reagent is 4 to 9.

13. The method according to claim 1, wherein the lysing reagent further comprises an alkyl dimethyl ethyl ammonium salt and an alkyl trimethyl ammonium salt having an alkyl group having a carbon number of 14.

14. A lysing reagent for classifying leukocytes in a canine or feline blood sample into a first group consisting essentially of lymphocytes, a second group consisting essentially of neutrophils and monocytes and a third group consisting essentially of eosinophils, comprising:
a quaternary ammonium salt lysing erythrocytes and shrinking leukocytes in the blood sample the quaternary ammonium salt comprising a first alkyl trimethyl ammonium salt having an alkyl group having a carbon number of 10 to 12 and a second alkyl trimethyl ammonium salt having an alkyl group having a carbon number of 16 to 18, and
an aqueous solvent dissolving the quaternary ammonium salt,
wherein the concentration of the quaternary ammonium salt is a concentration satisfying the following conditions:
(1) erythrocytes are sufficiently lysed, and
(2) leukocytes are shrunk such that the leukocytes can be classified, on the basis of their size, into the first, second and third groups.

15. The reagent according to claim 14, wherein the concentration of the quaternary ammonium salt is 1.5 mM to 20 mM.

16. The reagent according to claim 14, wherein
the first alkyl trimethyl ammonium salt is selected from a lauryl trimethyl ammonium salt, and
the second alkyl trimethyl ammonium salt is selected from the group consisting of a stearyl trimethyl ammonium salt and a cetyl trimethyl ammonium salt.

17. The reagent according to claim 16, wherein the concentration of the lauryl trimethyl ammonium salt is 8 to 20 mM, the concentration of the stearyl trimethyl ammonium salt is 0.4 to 2 mM, and the concentration of the cetyl trimethyl ammonium salt is 1.5 to 3 mM.

18. The reagent according to claim 14, which further comprises a nonionic surfactant having a Hydrophilic-Lipophilic-Balance value of 17 to 20.

19. The reagent according to claim 14, wherein the aqueous solvent is a buffer keeping the pH in the range of 4 to 9.

20. The reagent according to claim 14, wherein the quaternary ammonium salt further comprises an alkyl dimethyl ethyl ammonium salt.

21. A method for classifying leukocytes in animal blood, comprising the step of:
preparing a measurement sample by mixing a canine or feline blood sample with a lysing reagent, the lysing reagent comprising a first alkyl trimethyl ammonium salt having an alkyl group having a carbon number of 10 to 12 and a second alkyl trimethyl ammonium salt having an alkyl group having a carbon number of 16 to 18, wherein erythrocytes are lysed and leukocytes are shrunk in the measurement sample;
measuring data correlated with the size of leukocytes in the measurement sample;
classifying the leukocytes, on the basis of the measured data, into a first group consisting essentially of lymphocytes, a second group consisting essentially of neutrophils and monocytes and a third group consisting essentially of eosinophils; and
wherein the first, second and third groups appear in the order of small to large sizes based on the data correlated with the size of leukocytes.

* * * * *